United States Patent [19]

Bensimon et al.

[11] Patent Number: 6,130,044
[45] Date of Patent: *Oct. 10, 2000

[54] SURFACES FOR BIOLOGICAL REACTIONS, PROCESS FOR PREPARING THEM AND PROCESS FOR THEIR USE

[75] Inventors: David Bensimon, Paris; Aaron Bensimon, Antony; François Heslot, Viroflay, all of France

[73] Assignee: Institut Pasteur and Centre National de la Recherche Scientifique, Paris, France

[ * ] Notice: This patent is subject to a terminal disclaimer.

[21] Appl. No.: 09/084,004

[22] Filed: May 26, 1998

Related U.S. Application Data

[62] Division of application No. 08/693,098, filed as application No. PCT/FR95/00164, Feb. 10, 1995, abandoned.

[30] Foreign Application Priority Data

Feb. 11, 1994 [FR] France ................................. 94 01574
Jun. 17, 1994 [FR] France ................................. 94 07444

[51] Int. Cl.[7] ............................... C12Q 1/68; C12Q 1/70; G01N 33/53; G01N 33/48; G01N 33/01
[52] U.S. Cl. ........................ 435/6; 435/5; 435/6; 435/7.1; 435/970; 435/969; 436/63; 436/96; 436/501; 436/532; 524/511; 935/77; 935/78; 422/104
[58] Field of Search ................................. 436/63, 96, 532, 436/501; 435/5–6, 970, 969; 524/511; 935/77, 78; 422/104

[56] References Cited

U.S. PATENT DOCUMENTS

| | | |
|---|---|---|
| 4,539,061 | 9/1985 | Saqiv . |
| 4,562,157 | 12/1985 | Lowe et al. . |
| 5,019,416 | 5/1991 | Honzawa . |
| 5,102,798 | 4/1992 | Guiseppi-Elie . |
| 5,178,947 | 1/1993 | Charmot et al. . |
| 5,215,882 | 6/1993 | Bahl et al. . |
| 5,237,016 | 8/1993 | Ghosh et al. . |
| 5,330,891 | 7/1994 | Sutton . |
| 5,554,088 | 9/1996 | Whitehead et al. . |
| 5,610,287 | 3/1997 | Nikiforov et al. . |
| 5,624,711 | 4/1997 | Sudberg . |
| 5,677,126 | 10/1997 | Bensimon et al. ........................ 435/6 |
| 5,840,862 | 11/1998 | Bensimon et al. . |
| 5,846,724 | 12/1998 | Bensimon et al. ........................ 435/6 |
| 5,851,769 | 12/1998 | Gray et al. . |

FOREIGN PATENT DOCUMENTS

| | | |
|---|---|---|
| 0 125 995 | 11/1984 | European Pat. Off. . |
| 0 127 438 | 12/1984 | European Pat. Off. . |
| 0 388 940 | 9/1990 | European Pat. Off. . |
| 0 391 674 | 10/1990 | European Pat. Off. . |
| WO 97/06278 | 2/1997 | WIPO . |

OTHER PUBLICATIONS

Beattie et al., "Hybridization of DNA Targets . . . ", Biotechnology, 4:213–225 (1995).
A. Bensimon et al., "Alignment and Sensitvie Detection . . . " Science, 265 (5181) 2096–2098 (1994).
Lund et al., "Assessment of Methods for Covalent . . . ", Nucleic Acid Res., 16(22): 10861–10880 (1988).
Netzer et al., "A new Approach to Construction . . . ", J. Amer. Chem. Soc., 105(3): 674–676 (1983).
Tskhovreboa et al., "Direct Visualization of Extensibility in Isolated Titin Molecules", J. Mol. Biol., 265:100–06 (1997).

*Primary Examiner*—Jeffrey Stucker
*Assistant Examiner*—Padma Baskarr
*Attorney, Agent, or Firm*—Finnegan, Henderson, Farabow, Garrett & Dunner, L.L.P.

[57] ABSTRACT

A highly specific surface for biological reactions, which includes a support with at least one essentially compact layer of an organic compound. On the outside of the organic compound layer is an exposed group containing an ethylenic double bond, which has affinity for a molecule with biological activity under certain reaction conditions. The other elements of the organic compound layer are essentially inaccessible to the molecule with biological activity under the reaction conditions.

16 Claims, 6 Drawing Sheets

SURFACES FOR BIOLOGICAL REACTIONS, PROCESS FOR PREPARING THEM AND PROCESS FOR THEIR USE

CROSS REFERENCES TO RELATED APPLICATIONS

This application is a division of Ser. No. 08/693,098 filed Oct. 2, 1996, now abandoned, which is a §371 national phase filing of International Application No. PCT/FR95/00164, filed Feb. 10, 1995.

BACKGROUND OF THE INVENTION

The present invention relates especially to very highly specific surfaces which can be used in biology, as well as to their applications and to processes for preparing them.

The very high specificity and the very high selectivity of certain biological reactions, especially antigen/antibody reactions, DNA or RNA hybridization reactions, interprotein or avidin/streptavidin/biotin type reactions, as well as reactions of ligands and their receptors, have been known for a long time.

It is now known how to take advantage of these specificities, especially in order to detect the presence or the absence of one of the elements of the reaction pair in a sample or alternatively for separating one of the elements of the pair from a more complex medium.

However, when it is desired to detect the presence of a molecule at a very low concentration in a very complex medium, currently known processes sometimes give very unpredictable results given especially the problem of background noise which occurs during the separation and/or detection stages.

Consequently, what will be called hereinafter "molecular fishing", that is to say the possibility of being able to detect each of the searched-for molecules when they are at very low concentrations, has so far not been possible.

By way of example, the analysis of a DNA sample requires the use of a so-called "hybridization" probe corresponding to the sequence complementary to the desired sequence. Under these conditions, the problem posed is to isolate the hybrid from the medium and to detect, with a good signal/noise (S/N) ratio, the possibly reduced number of positive reactions.

Consequently, an intermediate stage intended to amplify the sought sequence is now used in most cases, for example using the PCR method or amplification methods which lead to the same results; under these conditions, the concentration of the sequence to be determined is increased in the sample and its detection is obviously much easier.

However, the amplification stage is sensitive to contaminants and leads to errors which are specific to it.

It would therefore be preferable, as far as possible, to be able to detect the presence of the nucleic acid sequence without an amplification phase.

It has been proposed to use, in order to detect the specific hybridization reaction, an intermediate stage of anchoring the hybridization product on a solid surface having certain specificities. For example, it is possible to use certain pretreated surfaces which make it possible to attach certain proteins or DNA, whether it has been modified or not.

Such surfaces are commercially available (Covalink, Costar, Estapor, Bangs, Dynal for example) in the form of beads or wells having at their surface COOH, $NH_2$ or OH groups for example.

It has also been proposed, in order to obtain such groups, to use an intermediate stage having a vinyl group which is then oxidized so as to have COOH or OH groups (U.S. Pat. No. 4,539,061 and EP 435 785).

It is then possible to functionalize the DNA with a reactive group, for example an amine, and to carry out a reaction with these surfaces. These methods require, however, a specific functionalization of the DNA to be attached.

A technique has also been described permitting the anchoring without prior treatment of the DNA. This process consists in reacting the free phosphate of the 5' end of the molecule with a secondary amine (NH Covalink surface).

It is also possible to attach the DNA to a group or a protein $P_0$ in order to cause it to react with a surface coated with a group or a protein $P_1$, which is capable of reacting specifically with $P_0$. The $P_0/P_1$ pair may be a pair of the following type: biotin/streptavidin or digoxigenin/antibody directed against digoxigenin (anti-DIG) for example.

Such surfaces are, however, in most cases insufficiently specific (V. Lund et al., Nucl. Acids Res., 16, 1861 (1988)). Thus, the presence of unwanted, even weak, interactions of the nonspecific adsorption type leads to efficient adsorptions for long molecules capable of forming, with the solid, a large number of points of weak interaction. These surfaces lead to potential applications which lack sensitivity and/or with a high level of background noise in the case of a small number of molecules to be fished out. Furthermore, some of these surfaces have a high level of unwanted fluorescence which is potentially disruptive during the detection phase.

As regards the detection itself, in particular for the detection of DNA, French Patent 78 10975 describes a process coupling the probe with an enzyme which allows revealing by means of a chromogenic substrate. It is, in addition, possible to quantify the reaction by a calorimetric measurement.

Such a technique is, however, not directly adapted to the detection of traces; consequently, here too, it should be preceded in most cases by an amplification stage for the desired quantity of nucleic acid, for example by the PCR method.

This so-called process of detection "by a cold probe" was developed in order to avoid the use of radioactive markers which yield results close in terms of sensitivity but which obviously present handling problems, given the presence of radioactive products and problems of long revealing times if a high sensitivity is desired.

For certain specific applications, especially methods derived from ex vivo imaging, there has been proposed a direct method for observing the reaction by coupling the product of the hybridization to microbeads, especially PMMA, polymethylmethacrylate, suitably treated chemically at their surface. The method is based on the direct identification, under a scanning electron microscope, of the presence of these microbeads with a typical diameter of 60 nm, and is furthermore based on known but insufficiently specific techniques for anchoring on solids, as described above.

The above techniques are obviously not limited to the detection of nucleic acids. In the same spirit, the detection of antibodies has been proposed. They are ELISA type tests which will not be described here and which, to summarize, make it possible to couple the presence of an antibody to an associated anchoring of a molecule of antigen on a solid. Again, the problems of specificity and unwanted reactions exist. The detection phase can then be based on a coupling to a chromogenic reaction having its own problems of sensitivity.

In summary, the prior art methods or combinations thereof have a number of disadvantages, in particular:

either of being potentially dangerous because of the use of radioactive products, or of requiring revealing times which are too long, or of being disrupted by specific problems at the level of the amplification phase, or of requiring solid surfaces which are not sufficiently specific or of being too weakly sensitive, or, finally, of requiring, in addition to the phase for attachment to a solid, the use of an electron microscope which is obviously not very convenient.

Finally, in most cases, the known processes do not make it possible to recognize, on a given molecule, the specific position of the desired unit. Now, this type of recognition is important when it is desired to perform mapping, in particular within the framework of genome mapping, it is desired to recognize, in a first instance, the approximate spatial position relative to one end of the molecule of a given gene on a DNA or an RNA.

SUMMARY OF THE INVENTION

The present invention, which proposes to overcome the disadvantages of the prior processes, is based on the use of very highly specific surfaces which, during their use, lead to excessively limited background noise, in particular because of the fact that they eliminate unwanted attachments.

BRIEF DESCRIPTION OF THE DRAWINGS

The descriptions that follow will be made with reference to the accompanying Figures in which.

DETAILED DESCRIPTION OF THE INVENTION

Figure 1:
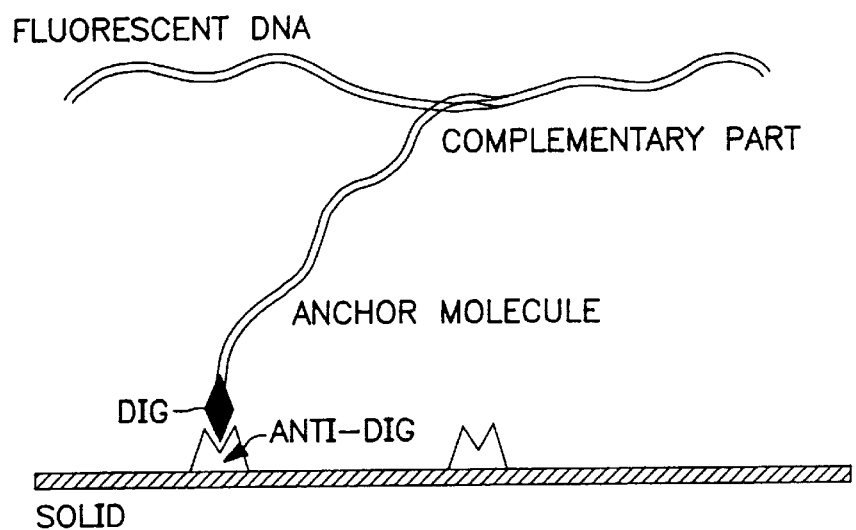
FIG. 1 schematically represents the detection of a pathogen by hybridization of fluorescently labeled DNA from the pathogen with an anchor molecule.

More particularly, the present invention relates to a highly specific surface for biological reactions, characterized in that it contains a support having at the surface at least one essentially compact layer of an organic compound having,
outside the layer, an exposed group containing an ethylenic double bond, especially a vinyl group, having affinity for one type of molecule with biological activity under certain reaction conditions, especially of pH or ionic content, the other elements of the layer being essentially inaccessible for the said molecules under the said reaction conditions.

By "affinity", there should be understood here both a chemical reactivity and an adsorption of any type, this under conditions for attachment of the said biological molecules.

By "support", it is intended to designate both a solid support and a support consisting of a nonsolid element such as a liquid or gaseous particle having, especially, a compact layer as described above.

The surface is "essentially compact", that is to say that it limits the access of the molecule with biological activity to the inner layers and/or to the support, it being understood that coating defects of the surface can be tolerated.

These highly specific surfaces for biological reactions, contain a support having at the surface groups with a double bond, especially vinyl (—CH=CH$_2$, hereinafter C=C surfaces) which are accessible to the solution. They are capable of directly anchoring molecules of biological interest (DNA, RNA, PNA, peanut agglutinin, proteins, lipids, saccharides) under certain conditions of pH or ionic content of the medium. In particular, these surfaces do not require specific chemical modification either of the surface or of the biological molecules to be anchored. There are no documents mentioning such a use of a surface with vinyl groups.

By "anchoring", there should be understood here an attachment by covalent linkage resulting from a chemical reactivity, or alternatively a noncovalent linkage resulting from physicochemical interactions such as an adsorption of any type, these under conditions of pH or ionic strength of the medium for the attachment of the said biological molecules.

The surfaces according to the present invention can be obtained using various processes. There may be mentioned by way of example:

(A) an optionally branched carbon-containing polymer layer, at least 1 nm thick, having:
  groups containing an ethylenic double bond,
  the remainder of the layer consisting of hydro- or fluorocarbon groups;

(B) surfaces obtained by depositing or anchoring on a solid one or more molecular layers, the latter can be obtained by the formation of successive layers attached by noncovalent bonds of the Langmuir-Blodgett film type, or by molecular self assembly, this permitting the formation of a layer attached by a covalent bond.

In the first case, the surface can be obtained by polymerization of at least one monomer generating at the surface of the polymer the said group containing an ethylenic double bond, or alternatively by partial depolymerization of the surface of a polymer so as to generate the said group, or alternatively by deposition of polymer.

In this process, the polymer formed has vinyl bonds like a polyene derivative, especially surfaces of the synthetic rubber type, such as polybutadiene, polyisoprene or natural rubber.

In the second case, the highly specific surface for biological reactions according to the present invention contains:
  on a support, a substantially monomolecular and compact layer of an organic compound of elongated structure having at least:
    an attachment group having affinity for the support, and
    an exposed group containing an ethylenic double bond, having little or no affinity for the said support and the said attachment group under the attachment conditions, but having affinity for one type of biological molecule.

In order to obtain essentially compact layer, the various organic compounds are preferably capable of reacting with each other besides the exposed group so as to create cross-linkages; an "essentially" compact monomolecular layer is thus obtained by virtue of which the support becomes inaccessible or barely accessible for unwanted reactions.

Preferably, the organic compound has an attachment group at one end and an exposed group at the other end. It is of course possible to consider various embodiments in which, for example, the attachment group would be situated in the middle of the molecule, the latter having an exposed group at each of its ends.

The surfaces can be analysed according to:
a) the support,
b) the molecule having an exposed group and an attachment group on the support,
c) the interaction between the support and the said molecule ensuring the attachment.

The attachment can first of all be of the non-covalent type, especially of the hydrophilic/hydrophilic and hydrophobic/hydrophobic type, as in Langmuir-Blodgett films (K. B. Blodgett, J. Am. Chem. Soc. 57, 1007 (1935) and U.S. Pat. No. 5,102,798).

In this case, the attachment group will be either hydrophilic or hydrophobic, especially alkyl or haloalkyl groups such as $CH_3$, $CF_3$, $CHF_2$, $CH_2F$.

The attachment can also be of the covalent type, the attachment group will, in this case, react chemically with the support.

Certain surfaces of similar structure have already been mentioned in the electronic field, especially when the attachments are covalent, L. Netzer and J. Sagiv, J. Am. Chem. Soc. 105, 674 (1983), and U.S. Pat. No. 4,539,061.

Persons skilled in the art have available a wide range of groups. By way of nonlimiting example, there may be mentioned groups of the metal alkoxide type, such as silane, silane chloride, ethoxysilane, methoxysilane.

The attachment group is obviously chosen as a function of the support used. The support according to the invention may consist, at least at the surface, of a polymer, a metal, a metal oxide, a semiconductor element or an oxide of a semiconductor element such as a silicon oxide or one combination thereof. Glass and surface-oxidized silicon can be mentioned in particular.

Among the attachment groups, there should be mentioned more particularly the groups of the metal alkoxide type such as silane, chlorosilane, chlorosilane, silanol, methoxysilane, ethoxysilane, silazane, phosphate, hydroxyl, hydrazide, hydrazine, anine, amide, diazonium, pyridine, sulfate, sulfonic, carboxylic, boronic, halogen, acid halide, aldehyde.

Most particularly, as attachment group, the use of groups capable of cross-reacting with an adjacent equivalent group to give cross-linkages, will be preferred; for example, this will be derivatives of the silane type, especially dichlorosilane, trichlorosilane, dimethoxysilane, trimethoxysilane, diethoxysilane and triethoxysilane.

These cross-linkages can also be performed at any point within the depth of the monolayer, by polymerizing it by means of reactive groups which may be present in the chain between the site of attachment and the exposed group. Thus, the diacetylenic groups are known to allow a uni- or two-dimensional polymerization of the mono-layer.

The choice of the attachment group will obviously depend on the nature of the support, the silane type groups are quite suitable for covalent bonding on glass and silica.

Preferably, the chains linking the exposed group to the attachment group are chains containing at least 1 carbon atom, preferably more than 6 and in general from 3 to 30 carbon atoms. When there is formation of a side coupling actually inside the layer, whether by ionic, coordination or covalent coupling, highly ordered layers are obtained which are obtained by self-assembly, even if the initial surface has only a limited number of active anchoring sites compared with the number of molecules obtained in a compact monolayer.

Known techniques for surface functionalization using silane derivatives, for example: $Si-OH + Cl_3-Si-R-CH=CH_2$ gives $Si-O-Si-R-CH=CH_2$, R consisting for example of $(CH_2)_4$, can be advantageously used in the case of glass or silica. Such a reaction is known in the literature, with the use of ultrapure solvents. The reaction leads to a layer of molecules having their C=C end at the surface exposed outside.

Within the framework of the production of a highly specific surface, the present invention also relates in the context of such reactions for grafting molecules with a C=C double bond to the use of a gaseous phase making it possible to avoid use of solvents.

In the case of gold, the latter being optionally in the form of a thin layer on a substrate, known techniques for surface functionalization use thiol derivatives, for example: $Au + HS-R-CH=CH_2$ gives $Au-S-R-CH=CH_2$, R consisting for example of $(CH_2)_4$. Such a reaction is described in a liquid medium and leads, like the preceding trichlorosilane-silica reaction, to a layer of molecules having their C=C end at the surface exposed outside.

Of course, the term "support" also covers both a single surface such as a slide, but also particles, whether silica powder or polymer beads, and also any forms such as bar, fiber or structured support, which can moreover be made magnetic, fluorescent or colored, as is known in various assay technologies.

Preferably, the support will be chosen in order not to be fluorescent or barely fluorescent when the detection will be carried out by fluorescence.

The surfaces obtained according to modes (A) or (B) above have a high specificity by virtue of the presence of specific reactive sites coming from the exposed groups or from the attached molecule.

In addition, the surfaces obtained according to modes (A) or (B) have the following unexpected and remarkable characteristics:

(i) a specific and highly pH-dependent anchoring of the DNA by its ends without requiring specific functionalization of the molecule, accompanied by a very low level of nonspecific interactions;

(ii) the possibility of anchoring on them proteins and other molecules of biological interest, without special chemical modification;

(iii) the possibility of preparing surfaces which are specific towards an antigen (for example digoxigenin) or a ligand (for example biotin);

(iv) a very low intrinsic fluorescence level, when required, a fluorescence background noise, (with a typical area of 100×100 μm) which is lower than the fluorescence signal of a single molecule to be detected;

(v) the possibility of detecting isolated molecules with an S/N ratio independent of the number of molecules, which is possible by virtue of various techniques with a high S/N ratio which are described below and which are based on identifying the presence of a macroscopic marker having a weak nonspecific interaction with the surface.

The surfaces thus obtained are preferably coated with a molecule with biological activity chosen from:
proteins,
nucleic acids
lipids
polysaccharides and derivatives thereof.

Among the proteins, there should be mentioned antigens and antibodies, ligands, receptors, but also products of the avidin or streptavidin type, as well as the derivatives of these compounds.

Among the RNAs and DNAs, there should also be mentioned the α, β derivatives as well as the thio derivatives and the mixed compounds such as PNAs.

Mixed compounds such as glycopeptides and lipopolysaccharides for example, or alternatively other elements such as viruses, cells in particular, or chemical compounds such as biotin, can also be attached.

The attachment of the biological molecules may be covalent or noncovalent, for example by adsorption, hydrogen bonding, hydrophobic or ionic interactions for example, in which case it will be possible to advantageously carry out cross-linking between the grafted molecules by known methods ("Chemistry of Protein Conjugation and Cross-linking", S. C. Wong, CRC Press (1991)) and this in order to enhance their cohesion.

With an exposed group containing a —CH=CH$_2$ radical which will be called hereinafter "C=C surface" or "surface with ethylenic bond", a direct anchoring, in particular of DNA or proteins is possible. Within the framework of the present invention, it has been demonstrated that these surfaces have a reactivity which is highly pH-dependent. This characteristic makes it possible to anchor the nucleic acids or the proteins, especially by their end(s), using a determined pH region and often with a reaction rate which can be controlled by the pH.

Thus, for DNA at pH 5.5, the anchoring reaction is complete in one hour (if it is not limited by diffusion) and occurs via the ends. At pH 8 on the other hand, the attachment is very low (reaction rate of 5 to 6 orders of magnitude smaller). This pH dependent attachment effect specific for the ends, is an improvement compared with the other surfaces which require functionalization of the DNA (biotin, DIG, NHS, and the like) or specific reagents (carbodiimide, dimethyl pimelidate) which form a peptide or phosphorimide linkage between —NH$_2$ and -COOR or —POOH.

The surfaces according to the invention can anchor proteins directly (protein A, anti-digoxigenin, antibodies, streptavidin, and the like). It has been observed that (i) the activity of the molecule can be preserved and (ii) that the reactivity of the prepared surface (initially C=C) is completely occulted in favor of the sole reactivity of the molecule of interest. It is therefore possible, starting with a relatively high initial reactivity, to pass to a surface having a very highly specific reactivity, for example that of specific sites on a protein.

By anchoring a specific antibody on the surface (for example anti-DIG), a surface is created whose reactivity is limited to the antigen (for example the DIG group). This indicates that the initial chemical groups have all been occulted by the antibodies anchored.

It is also possible to anchor onto the reactive (chemically or biochemically) surfaces other molecules with biological activity, especially viruses or other components: membranes, membrane receptors, polysaccharides, PNA, in particular.

It is also possible to attach the product of a reaction of biological interest (for example PCR) onto the prepared surfaces.

The present invention also relates to the surfaces obtained using the processes according to the present invention and all processes using this type of surface, whether they are processes permitting the detection and/or the quantification of biological molecules, but also the separation of certain biological molecules, especially a sample using antigen/antibody and/or DNA, DNA/RNA coupling techniques.

The present invention also relates to processes for preparing highly specific surfaces for biological reactions as described above for the production of layers according to (A) and (B) and, in particular, the process characterized in that:
a substantially monomolecular and compact layer of an organic compound of elongated structure having at least:
an attachment group having an affinity for the support, and
an exposed group containing an ethylenic double bond having no or little affinity for the said support and the attachment group under the attachment conditions, but having an affinity for one type of biological molecule, is attached onto a support.

The present invention also relates to the applications of the treated surfaces to the detection of isolated molecules by means of specific reagents and of detection methods with an S/N ratio independent of the number of molecules detected.

Thus, in general, the present invention relates to a process for detecting and/or assaying a molecule with biological activity in a sample, characterized in that a surface as described above, on which a molecule with biological activity capable of recognizing the sample molecule becomes attached, is used, and in that the detection or assay are carried out using a reagent, fluorescent or otherwise, which detects the presence of the attached molecule.

Among the reagents, there are fluorescent reagents and nonfluorescent reagents.

The fluorescent reagents contain fluorescent molecules, advantageously chosen to belong molecules of size greater than 0.1 µm and reacting specifically, directly or indirectly, with the pretreated surfaces. For example, but with no limitation being implied, a double-stranded DNA molecule stained by means of fluorescent probes (ethidium bromide, YOYO, a dimeric cyanine dye that fluoresces upon binding to nucleic acids, fluorescent nucleotides, and the like) capable of anchoring directly on a C=C surface, or by a modification of the molecule (DIG, biotin and the like) on a surface having complementary proteins (anti-DIG, streptavidin, and the like).

The nonfluorescent reagents consist especially of beads anchored via a molecule attached specifically, directly or indirectly, to a pretreated surface. By virtue of the surface treatment, these beads exhibit a weak nonspecific interaction with the surface. For example, but with no limitation being implied, Dynal beads coated with streptavidin and anchored via a biotinylated DNA to a surface according to the present invention, having sites capable of reacting with the other end of the DNA molecule.

Depending on whether the desired molecule is detected directly by fluorescence or indirectly by means of the above reagents, the detection will be described as "direct detection" or "flag detection".

In order to limit the problems associated with the prohibitively slow reaction times, the diffusion times of the reagents towards the surface can be advantageously reduced using small reaction volumes. For example, but with no limitation being implied, by carrying out the reaction in a volume of a few microliters determined by the space between two surfaces of which one is treated so as to have reactive sites according to the present invention and the other is inert or treated so as not to have reactive sites.

The detection of the number of specific reactions which have occurred can be carried out on a small number of molecules (typically 1 to 1000), by a low-noise macroscopic physical test requiring neither electron microscope nor radioactivity nor necessarily PCR.

The detection processes are capable of being carried out by persons having only limited laboratory experience.

Depending on the reagent, two implementations of the present invention (mode X and mode Y) can be used for the low-noise macroscopic detection of a small number of reactions for anchoring the reagent.

In the implementation of the so-called X mode of the present invention, a test of the number of specific reactions being produced is obtained directly by a fluorescence technique, which makes it possible, for some embodiments of the present invention, to individually identify the number of sites which have reacted. In this case, the highly specific surface is advantageously taken so as to have a very low fluorescence level; in particular the support should have a low fluorescence.

After anchoring the fluorescent reagent, the detection and counting of the possibly small number of anchoring reactions can be advantageously carried out by means of a fluorescence optical microscope using a lens with a wide numeric aperture, making it possible to locate either directly with the eye, or after signal acquisition, the number of anchored fluorescent molecules.

It is possible to advantageously carry out a scanning of the field of observation in order to explore a larger surface than the only fixed field.

In the implementation of the so-called Y mode of the present invention, a bead type (for example, fluorescent, magnetic, colored) macroscopic reagent is detected.

Such a technique is derived from Manning et al. in the sense that the reaction is revealed by the presence or the absence of the microbeads. In one embodiment, a new process comprises:

(i) the use of beads with specific reactivity,
(ii) the use of beads which are not nanoscopic in size but which are situated in the 0.1 $\mu$m–200 $\mu$m range, detectable by a macroscopic technique, and
(iii) the absence of nonspecific reaction between beads and surface due to the use of the product according to the present invention.

The number of these macroscopic beads each characterizing an anchoring reaction is then determined by a macroscopic physical method among which, but with no limitation being implied, there may be mentioned the diffusion of light on the beads, optical microscopy and the fluorescence of the beads.

The specificity of certain biological reactions may be limited. Thus, within the framework of the hybridization, the hybrids can be imperfect (reactions with other sites) while having a reduced number of pairing and therefore a lower quality of binding. The present invention also covers the possible use of a stage for testing the quality of the bonds obtained. This test makes it possible to dissociate the products which have paired in a weak nonspecific manner, by adsorption, hydrophobic forces, imperfect hydrogen bonds, imperfect hybridization, in particular.

Consequently, the invention also relates, in a detection or assay process as described above, to a process where the product of the reaction between the molecule with biological activity and the sample molecule is subjected to a stress in order to destroy the mismatches before the detection.

This process offers, in addition to the possibility of destroying the mismatched pairs, the possibility of orienting the coupling products, which facilitates the measurements or the observations.

It is thus possible to apply to the surfaces, after attachment of the complementary elements, a stress which may consist of the single or combined use of:

centrifugation, gradient of magnetic field applied to the non-fluorescent reagents taken, in this case, to include magnetizable or magnetic microbeads, stirring, liquid flow, meniscus passage, electrophoresis temperature variation and/or temperature gradient.

The number of systems to have maintained their integrity or to have become destroyed is then determined by the low-noise detection techniques described below.

It should be noted that using the surfaces according to the present invention, it is possible to orient the molecules after their attachment by at least one point by passage of the air/water meniscus, especially over DNA. Thus, it was observed that the passage of the air/water meniscus over DNA in solution and anchored at the surface, resulted in a uniform extension of the anchored molecules. They appear, in this case, in the open air in the form of elongated fluorescent rods. These elongated molecules are stable in the open air and can be observed even after several weeks, without showing apparent degradation.

These remarkable and unexpected observations suggest a possibility of counting the number of DNA molecules anchored at the surface: on the one hand, the surfaces not being highly fluorescent, the signal/noise (S/N) ratio is good, on the other hand, seeking a highly correlated object (rod shape), it is very easy to increase the S/N ratio. That is to say to ignore the dusts, the inhomogeneities which have no special spatial correlation. It should be noted that in solution, the molecules in the form of a random coil fluctuate thermally, thereby causing very high variations in their fluorescence signal gathered, in general, with a small depth of field and limiting their observation. The present invention also covers this alignment and immobilization technique which therefore allows the observation of isolated molecules with a very high S/N ratio.

It is remarkable that this ratio is independent of the number of molecules anchored. The SIN ratio posed by the detection of one molecule is the same as that for 10,000. Furthermore, this stretching technique makes it possible to easily discriminate between molecules of varying lengths.

It is advantageously possible to proceed to the following stages in order to further improve the S/N ratio:

The molecule being stationary, its fluorescence signal can be integrated.

Microscopic observation presents a reduced field (typically 100 $\mu$m×100 $\mu$m with a ×100 immersion lens, N.A.=1.25). For a 1 cm$^2$ sample, scanning can be carried out, or it is possible to envisage the use of lower magnification lenses (×10 or ×20) but with a high numerical aperture.

The rods being always parallel, it is possible to envisage an optical spatial filtration method in order to further increase the S/N ratio.

Other global fluorescence methods can be envisaged (EP # 103426).

The linearization of the molecules is observed both within the framework of a chemical grafting (C=C) and in the case of immunological type linkages (DIG/anti-DIG).

Once the surface is in the open air, the DNA molecules are stable (they maintain their integrity even after several weeks) and fluorescent. This property can be advantageously used in order to defer the anchoring stage and the locating/counting stage for the molecules anchored, if this detection is done for example, but without limitation being implied, by fluorescence microscopy. Such a use is covered by the present invention.

A double (or multi) fluorescence technique can possibly be used to improve the S/N ratio or to detect a double or multi-functionality.

It is possible to extend the air/water meniscus used here in order to stretch the molecule to other systems such as oil/water or water/surfactant/air, in particular.

It is possible to use a dynamic orientation of the molecules in solution anchored at one end, by electrophoresis or flow in one or more successive directions, it being thereby possible for such a technique to lead to the synchronous detection of the presence of molecules in a given direction, by analysis of the temporal variations of the fluorescence signal corresponding to a given direction (for example, but with no limitation being implied, by using a suitably arranged optical spatial filter permitting a preferential signal to be obtained for certain orientations of the observed molecules).

However, the observed results show that this technique, in its simplest version (stretching in a single direction, without synchronous detection) is much less efficient than the use of the meniscus.

The surfaces and/or the reagents and/or the detection techniques described in the present invention can be used for numerous applications, among which, but with no limitation being implied:

the identification of one or more elements for sequencing of DNA or RNA which can be advantageously used for the diagnosis of pathogens or genetic mapping;

the measurement of the size of DNA fragments which can be advantageously used for the genetic mapping;

the improvement of the sensitivity of the ELISA techniques with the possibility of detecting a small number (possibly less than 1000) of immunological reactions.

The identification of DNA/RNA sequences can be performed first by reacting in the solution volume the DNA/RNA molecules with complementary probes (for example by hybridization or by means of proteins specific for the "anchors") possess a reactive group (DIG, biotin, and the like) capable of anchoring specifically on a surface according to the present invention (having for example as anchoring site an anti-DIG antibody or streptavidin). The detection of the anchoring reaction can be carried out directly by detection of the fluorescence of the DNA molecule stained by fluorescent molecules (ethidium bromide, YOYO, fluorescent nucleotides) (FIG. 1). It can also be carried out indirectly by detection of a "flag molecule": a reagent according to the present invention capable of attaching to the DNA/RNA molecule (for example by hybridization, protein-DNA interaction, and the like), but having no affinity for the anchoring sites of the probe.

Figure 2:
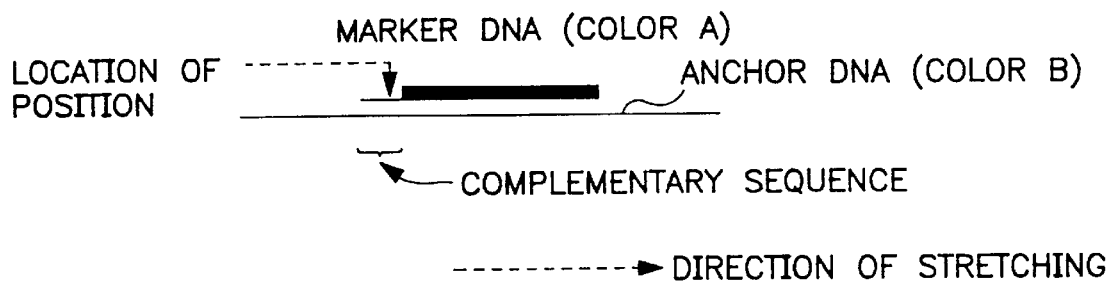
FIG. 2 schematically represents genetic mapping by extension of DNA and using a marker DNA.

In the "mapping" mode, the complementary probes can be directly coupled to a fluorescent reagent according to the present invention. It may be for example a single complementary DNA strand possessing bases modified so as to be fluorescent or a long double DNA strand stained with a fluorophore A and ending with a single strand segment complementary to the desired sequence. For different probes, fluorophores of different colors can be used. It is also possible to advantageously stain the DNA molecule to which the probes have just been hybridized with a fluorophore of a different color. The DNA-probe hybrid is anchored at one of its ends and stretched by one of the methods described above. The distance from the anchoring point to the hybridization points, or between the hybridization points, is determined by detecting the fluorescence of the probe, according to the methods described above (FIG. 2).

For example, with no limitation being implied, a marker DNA, of about 3000 base pairs and having at one of its ends a single strand segment complementary to the desired gene, is stained with a fluorophore A (for example YOYO1). This DNA is hybridized and then ligated with the single-stranded DNA to be mapped, and then the latter is stained with a second fluorophore B (POPO1), a dimeric cyanine dye with an adsorption/emission maxima of 434/456 nm when bound to nucleic acids, (after reacting by random priming, so as to convert it to a double-stranded DNA). The molecule is then anchored by one of its ends (for example by DIG/anti-DIG linkage) and stretched by the action of the meniscus. The distance between the end of the molecule and the position of the labeled gene, which can be observed by double fluorescence microscopy (2 colors A and B) makes it possible to establish the position of the desired gene with a precision of the order of 1000 base pairs (0.3 $\mu$m).

The identification of the DNA/RNA sequences can also be carried out by a reaction between the desired sequence and the reactive sites of a surface according to the present invention (for example complementary oligonucleotides or the site of reaction of a protein specific for the desired segment). The detection of the anchoring reaction can, in this case, be carried out directly or indirectly (by means of a "flag molecule") as described above.

It is well understood that the identification of the DNA/RNA sequences according to the present invention can serve both for diagnostic purposes (for example the detection of the presence or the absence of a viral or chromosomal pathogen) and for genetic mapping purposes. It can be preceded by an amplification stage by any method, especially PCR.

Moreover, as mentioned by K. R. Allan et al. (US 84 114), the genetic mapping can be carried out by measuring the size of the DNA fragments. Now, the coupling between the surfaces according to the present invention and the novel techniques for stretching the molecules described above (in particular and advantageously the stretching by the meniscus) makes it possible to measure the length of the stretched molecules and this on a very small sample (a few thousandths of molecules).

It is for example possible, with no limitation being implied, to carry out the process in the following manner:

A DNA sample is fragmented (by means of restriction enzymes) stained with a fluorophore and then anchored on a surface having reactive groups (for example the C=C surfaces). The molecules are then stretched by the meniscus and the size of the stretched fragments determined by fluorescence optical microscopy with a resolution and a maximum size of the order of 1000 bp (0.3 $\mu$m).

The surfaces according to the present invention can be used to carry out known processes which allow the detection and/or the quantification of an antigen or an antibody, especially the ELISA methods using enzymatic systems or RIA type methods using radioactive markers. These technologies will not be described in detail.

Figure 3:
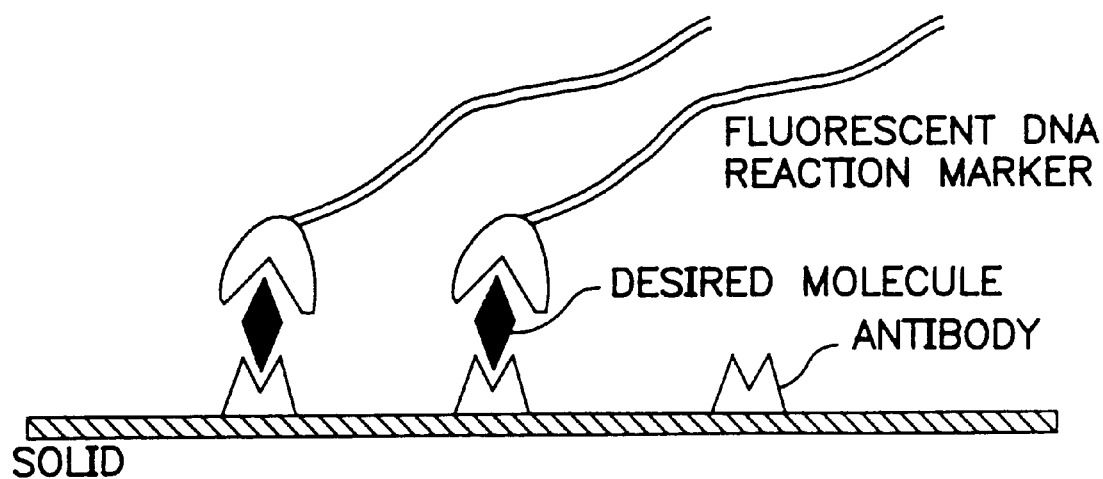
FIG. 3 schematically represents the detection of an immunological reaction (ELISA) by means of a "flag" molecule: a fluorescent DNA used as reaction marker.
Figure 4:
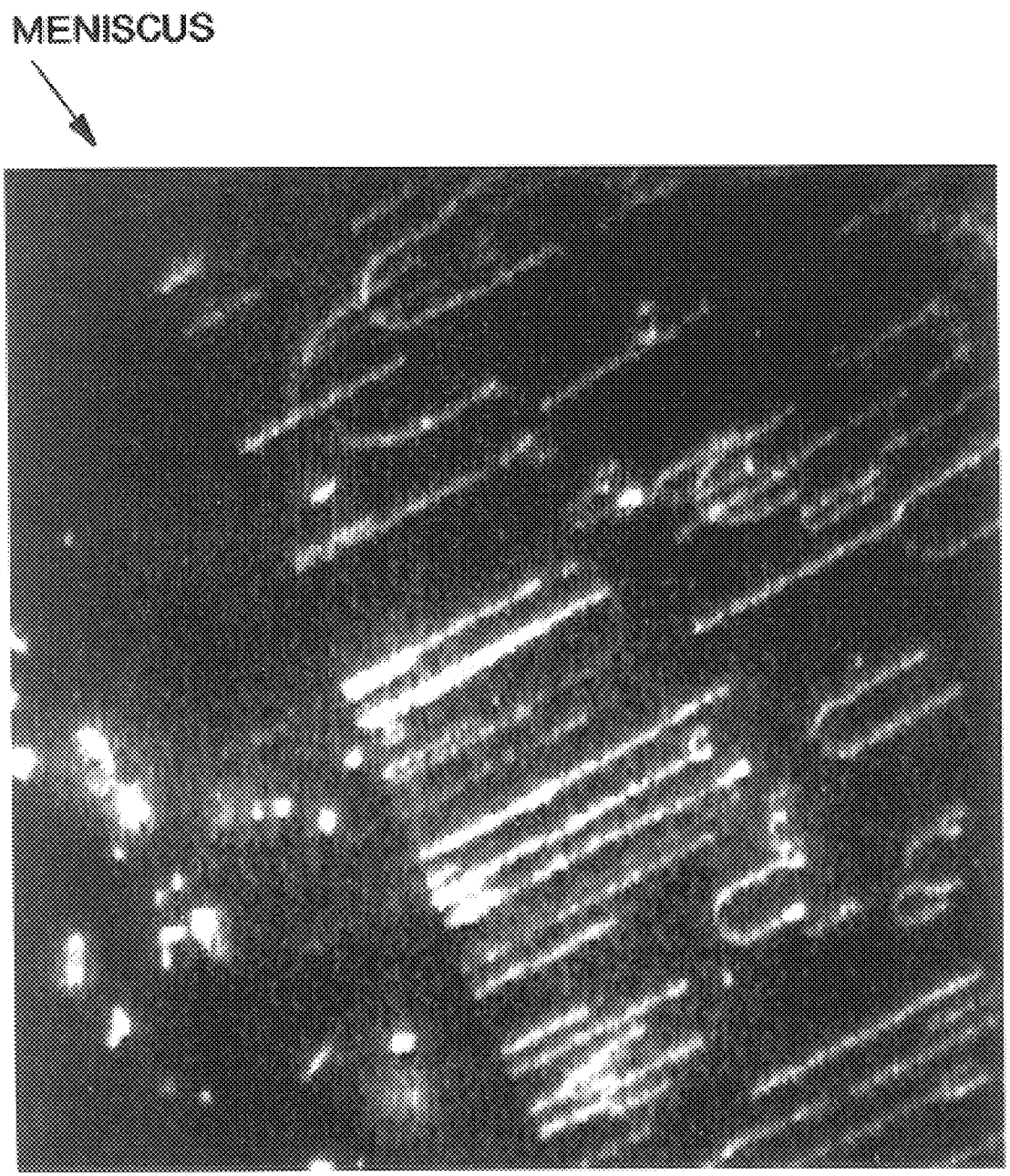
FIG. 4 is a fluorescence micrograph showing the extension of λ phage DNA by the progression of the meniscus, DNA molecules in solution stretched by evaporation flow parallel to the meniscus can be seen on the left, DNA molecules in the open air after being stretched perpendicularly to the meniscus can be seen on the right.
Figure 5A:
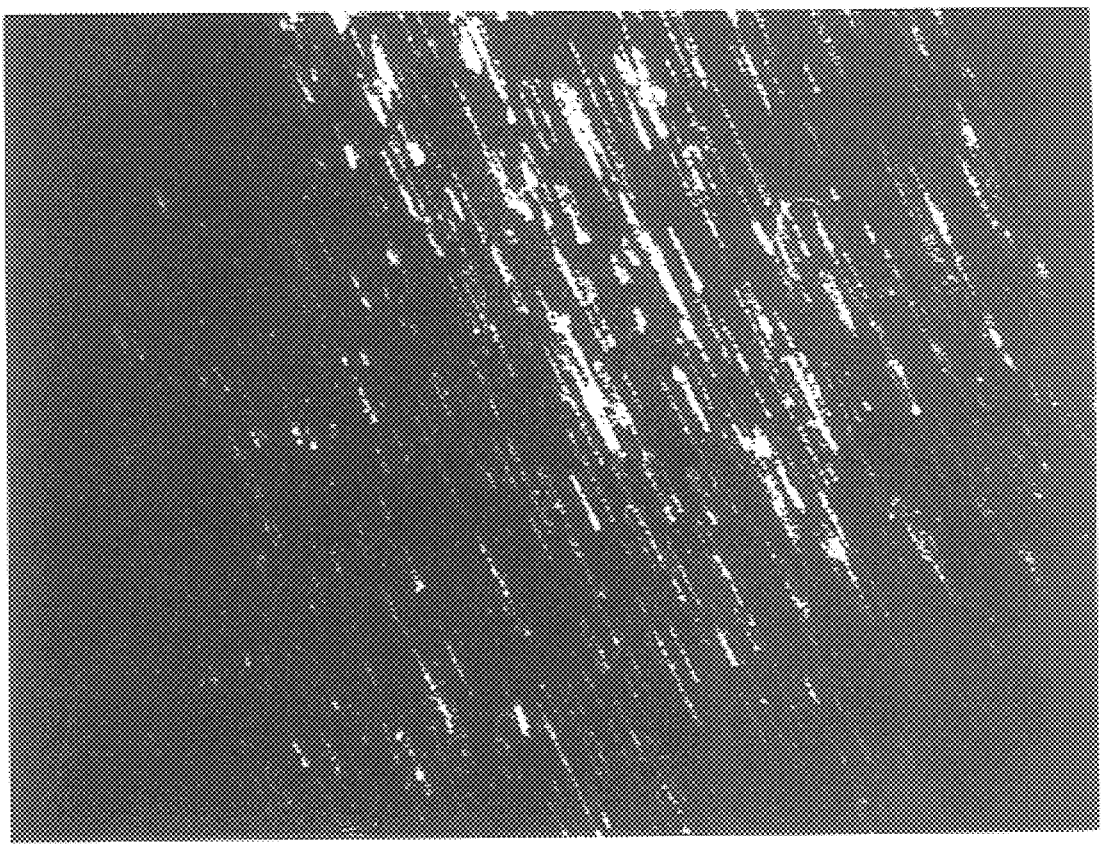
FIGS. 5(a) and 5(b) are fluorescence micrographs showing, respectively, a DNA labeled with digoxigenin (DIG) on a surface coated with anti-DIG and stretched by the meniscus, and, as control, an unlabeled DNA on an anti-DIG surface; the very high specificity of the surfaces and the absence of nonspecific anchoring will be noted.
Figure 5B:
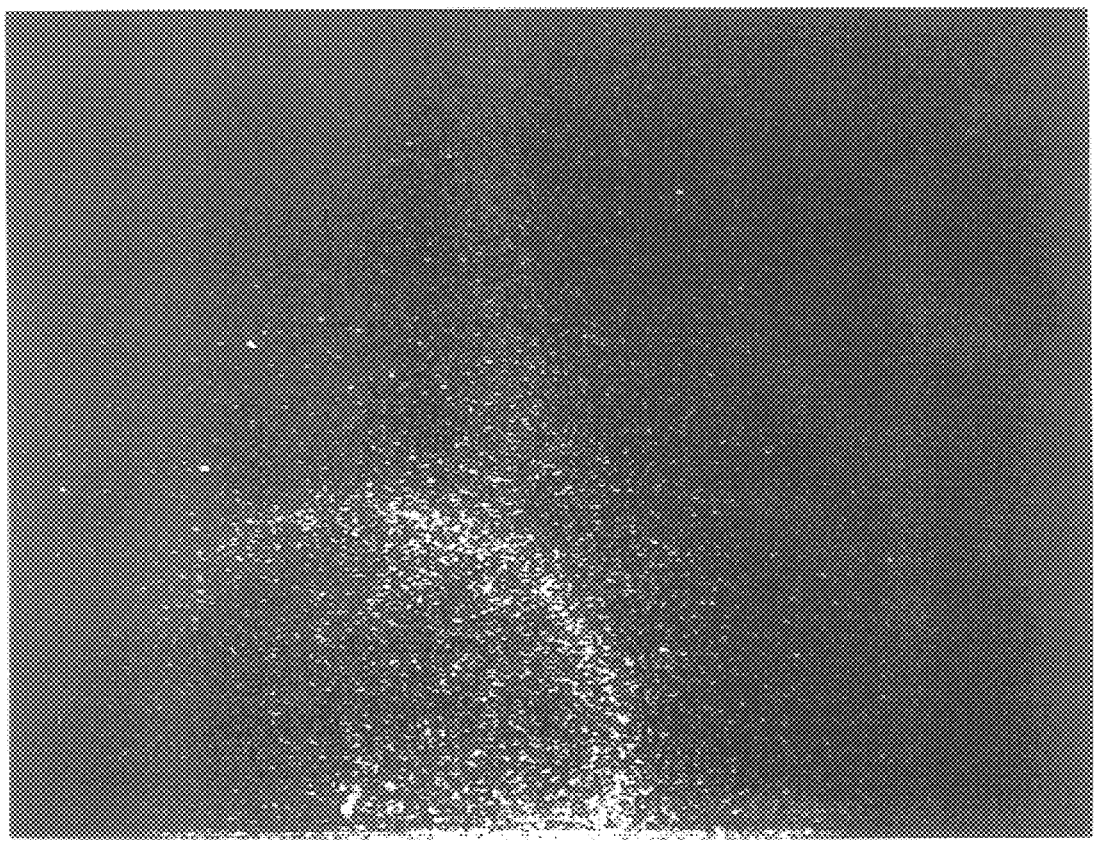
Figure 6:
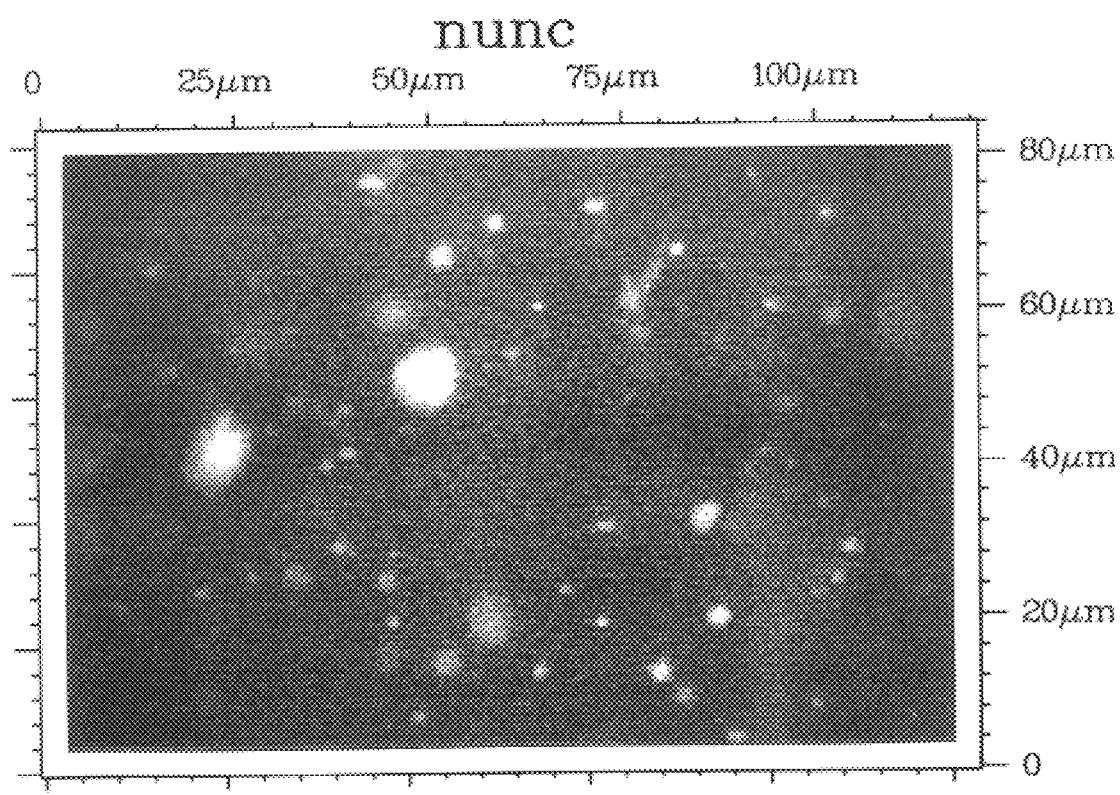
FIG. 6 is a fluorescence micrograph showing a conventional commercial surface, such as NUNC, the very high fluorescence inhomogeneities, which render these surfaces impossible to use for the fluorescent detection of a single molecule should be noted.

It is also possible and advantageous to use the surfaces according to the present invention as support for the immunological reactions of an ELISA process having a stage for anchoring a reagent according to the present invention ("flag") on one of the ELISA reagents (FIG. 3). The detection can naturally be carried out globally by measurement of fluorescence. It is also possible to count the number of reactions; this can be advantageously carried out according to the detection methods described in the present invention, in particular the extension by the meniscus, and this by virtue of the low level of fluorescence and nonspecific interaction of the product of the present invention. This allows the detection of a small number of reactions, possibly less than 1000, with an excellent S/N ratio.

It is therefore possible, by a minor modification of the sandwiched ELISA methods (antibody-antigen-modified antibody, for example biotinylated), to graft on the surface a reagent according to the present invention, for example fluorescent DNA anchored on streptavidin.

All the variants of the ELISA technique apply with a much better sensitivity. Techniques for global fluorescence measurement are already used to determine the quality of the ELISA reactions. However, the process according to the invention allows a better detection because it is sensitive to the fluorescence signal from a single molecule.

Of course, it is possible to use these surfaces as surfaces for the attachment of at least one product of a reaction of biological interest, by way of example, with no limitation being implied, products of the amplification reaction, whether PCR or a related method and, finally, it is possible to use this type of surfaces as support for an affinity chromatography, whether preparative or for detection.

In this case, it is for example possible to graft a given population of oligonucleotides on silica beads which will constitute the stationary phase of a chromatographic column.

The chromatography stage should allow a characteristic specificity of the column with respect to the eluents, for example a DNA mixture of which some have complementary sequences or sequences very close to the grafted oligonucleotide.

The present invention finally relates to the use of the surfaces according to the present invention in diagnostic or separation kits.

Other characteristics and advantages of the present invention will emerge on reading the examples below.

Materials and methods

The λ DNA and the monoclonal antibody (anti-DIG) are obtained from Boehringer-Mannheim. The trichlorosilanes are obtained from Roth-Sochiel. The fluorescent nucleic probes (YOYO1, a dimeric cyanine dye with an adsorption/emission maxima of 491/509 nm when bound to nucleic acids, YOYO3, a dimeric cyanine dye with an adsorption/emission maxima of 612/631 nm when bound to nucleic aicds, and POPO1) are obtained from Molecular Probes. The ultraclean glass cover slips are obtained from Erie Scientific (ESCO) cover slips). The magnetic particles are obtained from Dynal. The microscope is a Diaphot inverted microscope from NIKKON, equipped with a Xenon lamp for epifluorescence and a Hamnmatsu intensified CCD camera for the visualization.

Surface treatment

Glass cover slips are cleaned for one hour by UV irradiation under an oxygen atmosphere (by formation of ozone). They are then immediately placed in a desiccator previously purged of traces of water by an argon stream. A volume of about 100 to 500 $\mu$l of the appropriate trichlorosilane ($H_2C=CH-(CH_2)N-SiCl_3$ is introduced into the desiccator, from which the surfaces are removed after about 12 hours (n=6) or 1 hour (n=1). Upon taking out, the surfaces are clean and nonwetting.

The cover slips thus functionalized can react with proteins. A volume of 300 $\mu$l of an aqueous solution (20 $\mu$g/ml) of proteins (protein A, streptavidin, and the like) is deposited on a cover slip functionalized with a ($H_2C=CH-$) group. This cover slip is incubated for about two hours at room temperature, then rinsed three times in ultrapure water. The surfaces thus treated are clean and wetting. The surfaces treated with protein A can then react with an antibody, for example an anti-DIG antibody, by incubating in a solution of 20 $\mu$g/ml of antibody.

Anchoring of native DNA on a double bond surface

A drop of 2 $\mu$l of a fluorescence-labeled λ DNA solution (YOYO1, POPO1 or YOYO3, but with no specific end labeling) of varying concentration and in different buffers (total number of molecules $<10^7$) is deposited on a pre-treated cover slip ($H_2C=CH$) and covered with an untreated glass cover slip (diameter 15 mm). The preparation is incubated for about 1 hour at room temperature in an atmosphere saturated with water vapor. In a 0.05 M MES buffer (pH=5.5), a virtually general anchoring of the DNA molecules is observed. In contrast, in a 0.01 M Tris buffer (pH=8), there is practically no anchored molecule (ratio $>10^6$). This dependence can make it possible to control the activation/deactivation of surfaces (with respect to DNA) via the pH.

Detection of the anchoring by the action of the meniscus

By transferring the preceding preparation to a dry atmosphere, the solution, upon evaporating, will stretch the DNA molecules anchored on the surface, perpendicularly to the meniscus. The capillary force on the DNA molecule (a few tens of picoNewtons) is indeed sufficient to completely stretch the molecule (greater than the entropic elasticity forces), but too weak to break the bond between the end of the molecule and the treated surface. The DNA having been fluorescence labeled, the stretched molecules (total length about 22 $\mu$m) can be individually and easily observed. The anchoring between the surface and the DNA being limited to the ends, it was possible to stretch either DNA of λ phage, of YAC, yeast artificial chromosome, or of *E. coli* (total length greater than 400 $\mu$m). This DNA preparation, stretched, fluorescent and in the open air, is stable for several days and can be observed in a nondestructive manner, by epifluorescence (Nikkon Diaphot inverted microscope with a ×100 lens, O.N.: 1.25).

Detection of the anchoring by electrophoresis

An electrophoretic cell is formed by a paraffin ring (thickness of about 100 $\mu$m) taken between a treated cover slip and an untreated glass cover slip between which two platinum electrodes are inserted. The assembly is rigidly held together by briefly melting the paraffin ring. The DNA solution is introduced into this cell by capillarity through two openings left in the paraffin ring, then both openings in the paraffin are sealed. The incubation is carried out, as above, at room temperature. On applying a low voltage (few volts) between the two platinum electrodes, there is observed, by fluorescence, a movement of the free DNA molecules (a few tenths of microns per second) and an extension in the direction of the flow of the anchored molecules which can thus be easily and individually identified by epifluorescence microscopy.

Specific anchoring and detection

By treating the surfaces as described above with a specific monoclonal antibody, it is possible to control their specificity very precisely. Thus, the specificity of anti-DIG treated surfaces was tested in relation to λ DNA hybridized with an oligonucleotide complementary to one of the Cos ends and possessing a digoxigenin group (DIG) and in relation to nonhybridized DNA. In the first case, a virtually general extension of the anchored molecules, by the action of the meniscus, was observed. In the second case, only a few anchored DNA molecules (<10) were observed in the whole sample. It is therefore estimated that the specificity of the method according to the invention is greater than $10^6$.

Sensitivity of the detection

In order to determine the sensitivity of the detection method by extension of the meniscus, 2.5 µl drops of a solution of λ DNA in 0.05 M MES (pH=5.5) containing a total of $10^5$, $10^4$ and 1000 molecules, were deposited on double bonding surfaces. The anchoring is carried out as described above. The cover slips are then observed by epifluorescence microscopy to determine the density of the anchored molecules. The latter indeed corresponds to that estimated: about 4–6 DNA molecules per field of vision (100 µm×100 µm) for a total of $10^5$ DNA molecules. For the lowest concentration, it was possible to observe about 10 molecules extended by the action of the meniscus. This number is essentially limited by the large number of fields of vision required to cover the whole sample (about 25,000), which makes a manual search difficult, but it can be advantageously carried out automatically and with a weaker lens, but with a larger field. In conclusion, the sensitivity of the method according to the invention allows detection and individual counting of less than 1000 DNA molecules.

What is claimed is:

1. A surface for biological reactions, comprising a support having at least one essentially compact layer of an organic compound having, outside the layer, an exposed group containing an ethylenic double bond having affinity for a molecule with biological activity, wherein the remainder of the layer is essentially inaccessible to the molecule with biological activity and further wherein one end of the molecule with biological activity is attached to the surface.

2. The surface according to claim 1, wherein the molecule with biological activity is a protein, a nucleic acid, a lipid, or a polysaccharide.

3. The surface according to claim 1, wherein the molecule with biological activity is a protein, DNA, or RNA.

4. The surface according to claim 1, wherein the molecule with biological activity is an antibody, an antigen, a ligand, or a ligand receptor.

5. The surface according to claim 1, which is coated with a molecule with biological activity, wherein said surface is highly specific for a biological reaction.

6. The surface according to claim 5, wherein the molecule with biological activity is a protein, a nucleic acid, a lipid, or a polysaccharide.

7. A process for detecting a DNA sequence or a protein in a sample, comprising the steps of:

(A) contacting the sample with a surface according to claim 3, (B) binding the sample DNA sequence or protein with the surface to form a DNA/DNA, DNA/RNA, or protein/protein hybrid, (C) stretching said hybrid by physicochemical means in order to orientate said hybrid, and (D) detecting said stretched hybrid.

8. The process according to claim 7, wherein the hybrid is stretched by passage of a meniscus in the direction of the stretching.

9. The process according to claim 8, wherein the meniscus is an air/water meniscus.

10. The process according to claim 7, wherein the stretching is carried out by an electric field acting on the molecules or a magnetic field acting on a magnetizable or magnetic particle.

11. The process according to claim 7, wherein the stretching is carried out mechanically.

12. The process according to claim 7, further comprising the step of subjecting said hybrid to a stress so as to destroy the mismatches before detection.

13. The process according to claim 12, wherein the hybrid is stretched by passage of a meniscus in the direction of the stretching.

14. The process according to claim 13, wherein the meniscus is an air/water meniscus.

15. The process according to claim 12, wherein the stretching is carried out by an electric field acting on the molecules or a magnetic field acting on a magnetizable or magnetic particle.

16. The process according to claim 12, wherein the stretching is carried out mechanically.

* * * * *